(12) United States Patent
Boulle et al.

(10) Patent No.: US 8,679,513 B2
(45) Date of Patent: Mar. 25, 2014

(54) COSMETIC USE OF A JASMONIC ACID DERIVATIVE FOR TREATING THE HAIR AND THE SCALP

(75) Inventors: Christophe Boulle, Paris (FR); Maria Dalko, Versailles (FR)

(73) Assignee: L'Oreal, Paris (FR)

( * ) Notice: Subject to any disclaimer, the term of this patent is extended or adjusted under 35 U.S.C. 154(b) by 65 days.

(21) Appl. No.: 13/382,114

(22) PCT Filed: Jul. 1, 2010

(86) PCT No.: PCT/EP2010/059350
§ 371 (c)(1),
(2), (4) Date: Mar. 8, 2012

(87) PCT Pub. No.: WO2011/000903
PCT Pub. Date: Jan. 6, 2011

(65) Prior Publication Data
US 2012/0157527 A1    Jun. 21, 2012

Related U.S. Application Data

(60) Provisional application No. 61/213,723, filed on Jul. 7, 2009.

(51) Int. Cl.
*A61K 8/02*    (2006.01)

(52) U.S. Cl.
USPC .......................................... 424/401; 524/530

(58) Field of Classification Search
None
See application file for complete search history.

(56) References Cited

U.S. PATENT DOCUMENTS

2004/0029839 A1* 2/2004 Boulle et al. .................. 514/129
2007/0092467 A1* 4/2007 Rozot et al. .................. 424/70.1

FOREIGN PATENT DOCUMENTS

| EP | 1333021 A2 | 8/2003 |
| FR | 2921254 A1 | 3/2009 |
| WO | WO-02/080890 A2 | 10/2002 |
| WO | WO-2004/023897 A1 | 3/2004 |

OTHER PUBLICATIONS

Fukui et al., "Isolation of Plant Growth Regulators from Seeds of *Cucurbita pepo* L", Agricultural and Biological Chemistry, Japan Soc. for Bioscience, Biotechnology and Agrochem, Tokyo, JP, vol. 41, No. 1, Jan. 1, 1977.
Torii et al., "Evaluation of Antiandrogen Effect using SC-3 Celle", Shiga Res. Group, NOEVIR, Youkaichi, 527, Japan, vol. 21, No. 2 (1997), pp. 97-102.
International Search Report in counterpart Appln No. PCT/EP2010/059350 mailed Apr. 2, 2012.

* cited by examiner

*Primary Examiner* — Lezah Roberts
*Assistant Examiner* — Nannette Holloman
(74) *Attorney, Agent, or Firm* — Novak Druce Connolly Bove + Quigg LLP

(57) ABSTRACT

The present invention relates to the cosmetic use of jasmonic acid derivatives of formula (I)

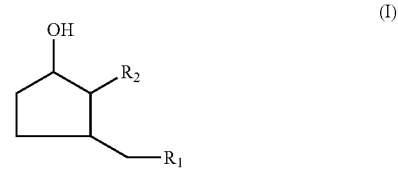

(I)

in which:

$R_1$ represents a radical $COOR_3$, $R_3$ denoting a hydrogen atom or a $C_1$-$C_4$ alkyl radical, optionally substituted with one or more hydroxyl groups;

$R_2$ represents a linear saturated or unsaturated hydrocarbon-based radical containing from 1 to 18 carbon atoms, or a branched or cyclic saturated or unsaturated hydrocarbon-based radical containing from 3 to 18 carbon atoms; and also an optical isomer thereof and/or a corresponding salt thereof, in a composition for caring for and/or making up keratin fibers, in particular human keratin fibers, for the purpose of inducing and/or stimulating the growth of the keratin fibers and/or of halting their loss and/or increasing their density.

8 Claims, No Drawings

COSMETIC USE OF A JASMONIC ACID DERIVATIVE FOR TREATING THE HAIR AND THE SCALP

CROSS-REFERENCE TO RELATED APPLICATIONS

This Application is a 35 U.S.C. 371 National Stage Application of International Application No. PCT/EP2010/059350, filed Jul. 1, 2010, claiming priority from French Patent Application No. 0954531, filed Jul. 2, 2009, and U.S. Provisional Application No. 61/213,723, filed Jul. 7, 2009, the entire contents of which are herein incorporated by reference.

FIELD OF THE INVENTION

The present invention relates to a novel family of jasmonic acid derivatives of formula (I) that will be defined in detail hereinbelow and to optical isomers thereof and/or the corresponding salts thereof and their use for the purpose of stimulating and/or inducing the growth of keratin fibres, especially human keratin fibres, and/or halting their loss and/or increasing their density.

BACKGROUND OF THE INVENTION

The human keratin fibres to which the invention applies are especially head hair, the eyebrows, the eyelashes, beard hairs, moustache hairs and pubic hairs. More especially, the invention applies to human head hair and/or eyelashes.

Hair growth and hair renewal are mainly determined by the activity of the hair follicles and of their matrix environment. Their activity is cyclical and comprises essentially three phases, namely the anagenic phase, the catagenic phase and the telogenic phase.

The anagenic phase (active phase or growth phase), which lasts several years and during which the hair gets longer, is followed by a very short and transient catagenic phase that lasts a few weeks. During this phase, the hair undergoes a change, the follicle becomes atrophied and its dermal implantation appears higher and higher.

The terminal phase or telogenic phase, which lasts a few months, corresponds to a resting phase of the follicle and the hair ends up falling out. At the end of this rest period, a new follicle is regenerated in situ and another cycle begins.

The head of hair is thus under permanent renewal, and, out of the approximately 150 000 hairs that make up a head of hair, about 10% are at rest and will be replaced within a few months.

The natural loss or falling-out of the hair may be estimated, on average, as being a few hundred hairs per day for a normal physiological state. This process of permanent physical renewal undergoes a natural change during ageing, the hairs become finer and their cycles shorter.

In addition, various causes may result in a substantial, temporary or permanent loss of hair. This may be loss and impairment of hair at the terminal stage of pregnancy (post-partum), during states of dietary malnutrition or imbalance, during physiological stress, or during states of asthenia or of hormonal dysfunction, as may be the case during or at the terminal stage of the menopause. It may also be a case of loss or impairment of the hair related to seasonal phenomena.

It may also be a matter of alopecia, which is essentially due to a disturbance in hair renewal, resulting, in a first stage, in acceleration of the frequency of the cycles to the detriment of the quality of the hair, and then of their quantity. The successive growth cycles result in hairs that are finer and finer and shorter and shorter, gradually transforming into an unpigmented down. Certain areas are preferentially affected, especially the temporal or frontal lobes in men, and a diffuse alopecia of the crown of the head is observed in women.

The term alopecia also covers a whole family of afflictions of hair follicles whose final consequence is the permanent, partial or general loss of the hair. This is more particularly a matter of androgenic alopecia. In a large number of cases, early loss of hair occurs in genetically predisposed individuals; this is then a matter of andro-chrono-genetic alopecia. This form of alopecia especially affects men.

In certain dermatoses of the scalp with an inflammatory component, for instance psoriasis or seborrhoeic dermatitis, hair loss may be greatly accentuated or may result in highly disrupted follicular cycles.

The colour of human hair and skin depends on various factors and especially on the seasons of the year, race, sex and age. It is mainly determined by the concentration of melanin produced by the melanocytes. These melanocytes are specialized cells that synthesize melanin via particular organelles, the melanosomes.

Melanin synthesis (or melanogenesis) is complex and schematically involves the following main steps:

Tyrosine ---->Dopa ---->Dopaquinone ---->Dopachrome ---->Melanin

Tyrosinase (monophenol dihydroxyl phenylalanine: oxygen oxidoreductase EC 1.14.18.1) participates in this sequence of reactions by especially catalysing the reaction for conversion of tyrosine into dopa (dihydroxyphenylalanine) and the reaction for conversion of dopa into dopaquinone.

The upper part of the hair follicle appears as a tubular invagination of the epidermis, which is buried just down to the deep layers of the dermis. The lower part, or hair bulb, itself comprises an invagination in which is found the dermal papilla. Around the dermal papilla, in the lower part of the bulb, is an area populated with cells with a high degree of proliferation (matrix cells). These cells are the precursors of the keratinized cells that will constitute the hair. The cells that result from the proliferation of these precursors migrate vertically in the bulb and become gradually keratinized in the upper part of the bulb; this assembly of keratinized cells will form the hair stem. Pigmentation of the hair and of other bodily hairs requires the presence of melanocytes in the bulb of the hair follicle. These melanocytes are in an active state, i.e. they synthesize melanins (or melanin pigments). These pigments are transferred to the keratinocytes intended to form the hair stem, which will give rise to the growth of a pigmented head hair or other bodily hair. This structure is known as a "follicular pigmentation unit".

It is known that, in the majority of populations, a brown skin coloration and maintenance of a constant coloration of head hair are important aspirations.

It is accepted that the appearance of grey or white bodily hairs and/or head hairs, or canities, is associated with a decrease in melanin in the hair stem. This phenomenon occurs naturally during the life of an individual. However, people are seeking to have a more youthful appearance and, with an aesthetic aim, they are often tempted to combat this phenomenon, especially when it occurs at a relatively early age.

One of the causes of hair loss, is oxidative stress induced especially by ultraviolet radiation. Although ultraviolet (UV) rays are known for transiently improving certain skin complaints, numerous literature data establish their role in oxidative stress and their involvement in accelerating ageing of the skin (photoageing). Ultraviolet radiation generates in the skin reactive oxygen species that damage cells by affecting the molecular and enzymatic antioxidant systems.

The skin, the scalp and the hair are the outermost organs of our body and are thus the first targets for environmental stress factors, most particularly represented by the ultraviolet radiation of sunlight, UVB and UVA.

Hair follicles are sensitive to the state of the extracellular matrix. Specifically, in the course of the successive hair cycles, the hair follicle is either in the upper part of the dermis (telogenic phase) or in the lower part of the dermis or hypodermis (anagenic phase). By way of example, perifollicular fibrosis participates in excessive hair loss in man (Yoo H. G. et al., 2006, Biol. Pharm. Bull., 29(6): 1246-1250).

Human hair follicles are also directly sensitive to oxidative stress: the studies described in the document by Arck et al., 2006, FASEB J., 20(9):1567-1569 demonstrate that oxidative stress impedes their growth and pigmentation.

Thus, the hair follicles directly or indirectly suffer the effects of oxidative stress. It thus appears important to seek to limit the formation of radical species in the skin and the scalp in order to limit excessive hair loss.

Novel active compounds are thus sought, which can induce or stimulate hair growth and/or reduce hair loss caused by oxidative stress induced especially by UV radiation.

Patent application WO 97/32562 discloses N-aryl-2-hydroxyalkylamides, patent application WO 98/05654 discloses 3-aryl-2,4-dioxooxazolidines, patent application EP 916 652 discloses N-aryl-2-hydroxyalkylamides and patent application WO 00/0 059 866 discloses benzoic acid ester derivatives, for stimulating or inducing hair growth and/or for stopping hair loss. These compounds pose stability or solubility problems in the supports of the compositions.

The Applicant has discovered a new family of compounds may especially be favourable towards stimulating and/or inducing the growth of keratin fibres, especially human keratin fibres, and/or towards halting their loss and/or increasing their density.

One subject of the present invention is the cosmetic use of at least one jasmonic acid derivative that will be defined in detail hereinbelow, and also an optical isomer thereof and/or a salt thereof, in a composition comprising a physiologically acceptable medium, for the purpose of inducing and/or stimulating growth of the keratin fibres, in particular human keratin fibres, and/or halting their loss and/or increasing their density.

Another subject of the present invention is a cosmetic process for the purpose of inducing and/or stimulating growth of the keratin fibres, in particular human keratin fibres, and/or halting their loss and/or increasing their density, consisting of applying a composition comprising in a physiologically acceptable medium, at least one jasmonic acid derivative that will be defined in detail hereinbelow, and also an optical isomer thereof and/or a salt thereof.

The term "skin" means any cutaneous surface of the human body, including skin, mucous membranes and semi-mucous membranes, thus including the lips, the scalp and also the skin's appendages, especially the nails, bodily hair and head hair.

According to the invention, a "physiologically acceptable medium" is either a medium that is cosmetically or pharmaceutically acceptable and compatible with the skin, mucous membranes, the nails and/or the hair, or a medium that can be administered orally.

The term "keratin fibres" means those of mammals of the animal species (for example dogs, horses or cats).

For the purposes of the invention, the term "human keratin fibres" means head hair, the eyebrows, the eyelashes, beard hair or moustache hair.

Other subjects of the invention will be defined later in the rest of the description.

The compounds according to the invention are represented by formula (I) below:

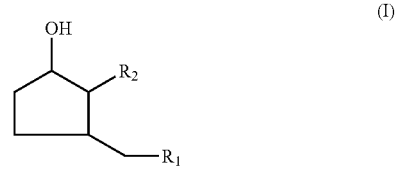

in which:

$R_1$ represents a radical $COOR_3$, $R_3$ denoting a hydrogen atom or a $C_1$-$C_4$ alkyl radical, optionally substituted with one or more hydroxyl groups;

$R_2$ represents a linear saturated or unsaturated hydrocarbon-based radical containing from 1 to 18 carbon atoms, or a branched or cyclic saturated or unsaturated hydrocarbon-based radical containing from 3 to 18 carbon atoms;

and also the optical isomers thereof, and corresponding salts thereof.

Preferably, $R_1$ denotes a radical chosen from —COOH, —COOMe, —COO—$CH_2$—$CH_3$, —COO—$CH_2$—CH(OH)—$CH_2$OH, —COO$CH_2$—$CH_2$—$CH_2$OH and —COO$CH_2$—CH(OH)—$CH_3$. Preferentially, $R_1$ denotes a radical —COOH.

Preferentially, $R_2$ denotes a saturated or unsaturated linear hydrocarbon-based radical, preferably containing from 2 to 6 carbon atoms. In particular, $R_3$ may be a pentyl, pentenyl, hexyl or heptyl radical.

The salts of the compounds that may be used according to the invention are chosen in particular from the salts of alkali metals, for example sodium or potassium; the salts of alkaline-earth metals, for example calcium, magnesium or strontium, metal salts, for example of zinc, aluminium, manganese or copper; ammonium salts of formula $NH_4^+$; quaternary ammonium salts; salts of organic amines, for instance methyl-amine, dimethylamine, trimethylamine, triethylamine, ethylamine, 2-hydroxyethylamine, bis(2-hydroxyethyl)-amine or tris(2-hydroxyethyl)amine salts; lysine or arginine salts. Salts chosen from those of sodium, potassium, calcium, magnesium, strontium, copper, manganese and zinc are preferably used.

According to one embodiment, the compound of formula (I) is chosen from 3-hydroxy-2-[(2Z)-2-pentenyl]cyclopentaneacetic acid or 3-hydroxy-2-pentyl-cyclopentaneacetic acid or a corresponding salt thereof, and is preferably 3-hydroxy-2-pentylcyclo-pentaneacetic acid and especially the sodium salt of 3-hydroxy-2-pentylcyclopentaneacetic acid.

The compounds of formula (I) are known per se and have been described and synthesized in patent application EP 1 333 021.

Thus, the invention also relates to the cosmetic use of at least one jasmonic acid derivative of formula (I), and also an optical isomer thereof and/or a salt thereof, in a cosmetic composition for human hair care, for the purpose of treating alopecia of natural origin and in particular androgenic alopecia. Thus, this composition can maintain the hair in good condition and/or can combat natural hair loss, more especially in the case of men. This composition can thus maintain the hair in good condition and/or improve its condition and/or its appearance.

A subject of the present invention is a cosmetic process for inducing and/or stimulating growth of the human keratin fibres (especially the hair or the eyelashes) including the scalp and the eyelids characterized in that it consists in applying to the said keratin fibres a cosmetic composition comprising in a physiologically acceptable medium, at least one jasmonic acid derivative of formula (I), and also an optical isomer thereof and/or a salt thereof, in leaving it in contact with the keratin fibres and optionally in rinsing the said fibres and/or the said skin.

This treatment process does indeed have the characteristics of a cosmetic process in so far as it makes it possible to improve the aesthetic appearance of human keratin fibres and especially the hair and the eyelashes by giving them greater vigour and an improved appearance. In addition, it may be used daily for several months, without medical prescription.

A subject of the present invention is a cosmetic process for inducing and/or stimulating growth of the eyelashes and/or halting their loss and/or increasing their density, characterized in that it consists in applying on the eyelashes and/or eyelids a mascara composition comprising in a physiologically acceptable medium, at least one jasmonic acid derivative of formula (I), and also an optical isomer thereof and/or a salt thereof, in leaving it in contact with the on the eyelashes and/or eyelids. This mascara composition may be applied alone or as a base coat for a standard pigmented mascara and may be removed like a standard pigmented mascara.

DETAILED DESCRIPTION OF EMBODIMENTS OF THE INVENTION

In the text hereinbelow, and unless otherwise mentioned, the use of the term "compound of formula (I)" should be understood as meaning not only the compound of formula (I), but also an isomeric form thereof and/or a salt thereof.

The effective amount of a compound of formula (I) corresponds to the amount necessary to obtain the desired result (namely to increase the density of keratin fibres and in particular of the hair or the eyelashes or to promote their growth or reduce their loss). A person skilled in the art is therefore capable of evaluating this effective amount, which depends on the nature of the compound used, on the individual to whom it is applied and on the length of time of this application.

In the text hereinbelow, and unless otherwise indicated, the amounts of the various ingredients in the composition are given as weight percentages relative to the total weight of the composition.

To give an order of magnitude, according to the invention, the compound of formula (I) or a mixture of compounds of formula (I) may be used in an amount ranging from $10^{-3}\%$ to 10% of the total weight of the composition, preferably in an amount representing from $10^{-3}\%$ to 5% and better still from $10^{-2}\%$ to 2% of the total weight of the composition, for example from 0.5% to 2%.

The composition of the invention may be for cosmetic or pharmaceutical use. The composition of the invention is preferably for cosmetic use. In addition, the composition must contain a non-toxic, physiologically acceptable medium that can be applied to human skin, including the scalp and the eyelids, and to human keratin fibres.

For the purposes of the invention, the term "cosmetic" means a composition of pleasant appearance, odour and feel.

The compound of formula (I) (salified or non-salified, and solvated or non-solvated) may be used in a composition that is to be ingested, injected or applied to the skin or to keratin fibres (to any area of skin or fibres to be treated).

According to the invention, the compound of formula (I) or a mixture of compounds of formula (I) may be used orally in an amount of from 0.1 to 300 mg per day, in particular from 5 to 10 mg/day.

A preferred composition of the invention is a composition for cosmetic use and in particular for topical application to the skin and keratin fibres, and more especially to the scalp, the hair and the eyelashes.

This composition may be in any known presentation form that is suitable for the mode of use.

For topical application to the keratin fibres, the composition may be in the form of an aqueous, alcoholic or aqueous-alcoholic solution or suspension, or an oily suspension or solution, an emulsion or dispersion of more or less fluid consistency and especially of liquid or semi-liquid consistency, obtained by dispersion of a fatty phase in an aqueous phase (O/W) or conversely (W/O), a solid (O/W) or (W/O) emulsion or dispersion, a more or less fluid or solid aqueous, aqueous-alcoholic or oily gel, a free or compacted powder to be used in unmodified form or to be incorporated into a physiologically acceptable medium, or alternatively microcapsules, microparticles or vesicular dispersions of ionic and/or nonionic type.

A composition in the form of a foam or alternatively in the form of a spray or aerosol, then comprising a pressurized propellant, may also be envisaged.

It may thus be in the form of a lotion, serum, milk, O/W or W/O cream, gel, unguent, ointment, powder, balm, patch, impregnated pad, cake or foam.

In particular, the composition for application to the scalp or the hair may be in the form of a haircare lotion, for example for daily or twice-weekly application, a shampoo or a hair conditioner, in particular for twice-weekly or weekly application, a liquid or solid scalp cleansing soap for daily application, a hairstyle shaping product (lacquer, hair setting product or styling gel), a treatment mask, a foaming gel or cream for cleansing the hair. It may also be in the form of a hair dye or mascara to be applied with a brush or a comb.

Moreover, for application to the eyelashes or bodily hair, the composition to which the invention applies may be in the form of a pigmented or unpigmented mascara, to be applied with a brush to the eyelashes or alternatively to beard or moustache hair.

For a composition for use by injection, the composition may be in the form of an aqueous lotion or an oily suspension. For oral use, the composition may be in the form of capsules, granules, drinkable syrups or tablets.

According to one particular embodiment, the composition according to the invention is in the form of a hair cream or hair lotion, a shampoo, a hair conditioner, a hair mascara or an eyelash mascara.

The amounts of the various constituents of the composition according to the invention are those generally used in the fields under consideration. In addition, these compositions are prepared according to the usual methods.

When the composition is an emulsion, the proportion of the fatty phase may range from 2% to 80% by weight and preferably from 5% to 50% by weight relative to the total weight of the composition. The aqueous phase is adjusted as a function of the content of fatty phase and of compound(s) (I) and also of that of the optional additional ingredients, to obtain 100% by weight. In practice, the aqueous phase represents from 5% to 99.9% by weight.

The fatty phase may contain fatty or oily compounds that are liquid at room temperature (25° C.) and atmospheric pressure (760 mmHg), which are generally known as oils. These oils may be mutually compatible or incompatible and may form a macroscopically homogeneous liquid fatty phase or a two-phase or three-phase system.

In addition to the oils, the fatty phase may contain waxes, gums, lipophilic polymers or "pasty" or viscous products containing solid parts and liquid parts.

The aqueous phase contains water and optionally an ingredient that is miscible in all proportions with water, for instance $C_1$ to $C_8$ lower alcohols such as ethanol or isopropanol, polyols, for instance propylene glycol, glycerol or sorbitol, or alternatively acetone or ether.

The emulsifiers and co-emulsifiers used to obtain a composition in emulsion form are those generally used in cosmetics and pharmaceuticals. Their nature also depends on the sense of the emulsion. In practice, the emulsifier and, where appropriate, the co-emulsifier are present in the composition in a proportion ranging from 0.1% to 30% by weight, preferably from 0.5% to 20% by weight and better still from 1% to 8% by weight. The emulsion may also contain lipid vesicles and especially liposomes.

When the composition is in the form of an oily solution or gel, the fatty phase may represent more than 90% of the total weight of the composition.

Advantageously, for a topical hair application, the composition is an aqueous, alcoholic or aqueous-alcoholic solution or suspension and better still a water/ethanol solution or suspension. The alcoholic fraction may represent from 5% to 99.9% and better still from 8% to 80%.

For a topical mascara application, the composition of the invention is especially in the form of a wax-in-water or wax-in-oil dispersion, a gelled oil or an aqueous gel, which may be pigmented or unpigmented.

The composition of the invention may also comprise other additional ingredients usually used in the fields under consideration, chosen from solvents, aqueous-phase or oily-phase thickeners or gelling agents, dyestuffs that are soluble in the medium of the composition, solid particles such as fillers or pigments, antioxidants, preserving agents, fragrances, electrolytes, neutralizers, film-forming polymers, UV blockers, for instance sunscreens, cosmetic and pharmaceutical active agents with a beneficial effect on the skin or keratin fibres, other than the compounds of formula (I), and mixtures thereof. These additives may be present in the composition in the amounts generally used in cosmetics and dermatology, and especially in a proportion of from 0.01% to 50% and better still from 0.1% to 20%, for example from 0.1% to 10%, relative to the total weight of the composition. Depending on their nature, these additives may be introduced into the fatty phase, into the aqueous phase and/or into the lipid vesicles and especially liposomes.

Needless to say, a person skilled in the art will take care to select the optional additional ingredients and/or the amount thereof such that the advantageous properties of the composition according to the invention, i.e. the increase in the density and/or the reduction in the loss of keratin fibres, are not, or are not substantially, adversely affected by the envisaged addition.

As solvents that may be used in the invention, mention may be made of $C_2$ to $C_8$ lower alcohols, for instance ethanol, isopropanol, propylene glycol and certain light cosmetic oils, for instance $C_6$ to $C_{16}$ alkanes.

As oils that may be used in the invention, mention may be made of oils of mineral origin (liquid petroleum jelly or hydrogenated isoparaffin), oils of plant origin (liquid fraction of Shea butter, sunflower oil, apricot oil, fatty alcohol or fatty acid), oils of animal origin (perhydrosqualene), synthetic oils (fatty acid ester, purcellin oil), silicone oils (linear or cyclic polydimethylsiloxane, phenyl trimethicone) and fluoro oils (perfluoropolyethers). Waxes that may be mentioned include silicone waxes, beeswax, rice wax, candelilla wax, carnauba wax, paraffin wax and polyethylene wax.

As emulsifiers that may be used in the invention, examples that may be mentioned include glyceryl stearate, glyceryl laurate, sorbitol stearates, sorbitol oleates, alkyl dimethicone copolyols (with alkyl $\geq 8$) and mixtures thereof for a W/O emulsion. Polyethylene glycol monostearate or monolaurate, polyoxyethylenated sorbitol stearate or oleate, and dimethicone copolyols, and mixtures thereof, may also be used for an O/W emulsion.

According to one particular embodiment of the invention, the compound of formula (I) or a salt thereof and/or an optical isomer thereof may be combined with additional compounds that promote the induction and/or stimulation of pigmentation of keratin materials and/or the limitation of their depigmentation and/or their whitening, for instance ellagic acid or Black Showu.

According to one particular embodiment of the invention, the compound of formula (I) or a salt thereof and/or an optical isomer thereof may be combined with additional compounds that promote the growth and/or limit the loss and/or increase the density of keratin fibres (hair or eyelashes). These additional compounds are chosen especially from the lipoxygenase inhibitors as described in EP 648 488, the bradykinin inhibitors described especially in EP 845 700, prostaglandins and derivatives thereof, especially those described in WO 98/33497, WO 95/11003, JP 97-100 091 and JP 96-134 242, prostaglandin receptor agonists or antagonists, the non-prostanoic prostaglandin analogues as described in EP 1 175 891, EP 1 175 890, WO 01/74307, WO 01/74313, WO 01/74314, WO 01/74315 or WO 01/72268, and mixtures thereof.

As other additional active compounds that promote the growth of keratin fibres and/or limit their loss (particularly the hair and the eyelashes), which may be present in the composition according to the invention, mention may be made of vasodilators, antiandrogens, cyclosporins and analogues thereof, antimicrobial and antifungal agents, anti-inflammatory agents, and retinoids, alone or as a mixture.

The vasodilators that may be used are especially potassium-channel agonists, including minoxidil, and also the compounds described in U.S. Pat. Nos. 3,382,247, 5,756,092, 5,772 990, 5,760,043, 5,466,694, 5,438,058 and 4,973,474, cromakalim, nicorandil and diazoxide, alone or in combination.

The antiandrogens that may be used especially include steroidal or non-steroidal 5α-reductase inhibitors, for instance finasteride and the compounds described in U.S. Pat. No. 5,516,779, cyprosterone acetate, azelaic acid and the salts and derivatives thereof, and the compounds described in U.S. Pat. No. 5,480,913, flutamide, oxendolone, spironolactone, diethylstilbestrol and the compounds described in U.S. Pat. Nos. 5,411,981, 5,565,467 and 4,910,226.

The antimicrobial or antifungal compounds may be chosen from selenium derivatives, octopirox, triclocarban, triclosan, zinc pyrithione, itraconazole, asiatic acid, hinokitiol, mipirocine, tetracyclines, especially erythromycin and the compounds described in EP 0 680 745, clindamycin hydrochloride, benzoyl peroxide or benzyl peroxide, minocycline and compounds belonging to the imidazole class, such as econazole, ketoconazole or miconazole or salts thereof. Nicotinic acid esters, especially including tocopheryl nicotinate, benzyl nicotinate and $C_1$-$C_6$ alkyl nicotinates, for instance methyl nicotinate or hexyl nicotinate, may be combined.

The anti-inflammatory agents may be chosen from steroidal anti-inflammatory agents, for instance glucocorticoids, corticosteroids (for example: hydrocortisone) and non-steroidal anti-inflammatory agents, for instance glycyrrhetinic acid and α-bisabolol, benzydamine, salicylic acid and the compounds described in EP 0 770 399, WO 94/06434 and FR 2 268 523.

The retinoids may be chosen from isotretinoin, acitretin, tazarotene, retinal and adapalene.

As other additional active compounds for promoting the growth and/or limiting the loss of keratin fibres such as the hair and the eyelashes, that may be used in combination with the compound of formula (I), mention may be made of aminexil, 6-0-[(9Z,12Z)octadeca-9,12-dienoyl]hexapyranose, benzalkonium chloride, benzethonium chloride, phenol, oestradiol, chlorpheniramine maleate, chlorophylline derivatives, cholesterol, cysteine, methionine, menthol, peppermint oil, calcium pantothenate, panthenol, resorcinol, protein kinase C activators, glycosidase inhibitors, glycosaminoglycanase inhibitors, pyroglutamic acid esters, hexosaccharidic or acylhexosaccharidic acids, substituted arylethylenes, N-acylamino acids, flavonoids, ascomycin derivatives and analogues, histamine antagonists, saponins, proteoglycanase inhibitors, oestrogen agonists and antagonists, pseudoterines, cytokines, growth factor promoters, IL-1 or IL-6 inhibitors, IL-10 promoters, TNF inhibitors, benzophenones, hydantoin, retinoic acid; vitamins, for instance vitamin D, vitamin B12 analogues and pantothenol; triterpenes, for instance ursolic acid and the compounds described in U.S. Pat. No. 5,529,769, U.S. Pat. No. 5,468,888 and U.S. Pat. No. 5,631,282; antipruriginous agents, for instance thenaldine, trimeprazine or cyproheptadine; antiparasitic agents, in particular metronidazole, crotamiton or pyrethrinoids; calcium antagonists, for instance cinnarizine, diltiazem, nimodipine, verapamil, alverine and nifedipine; hormones such as oestriol or its analogues, thyroxine and its salts, and progesterone; FP receptor (type-F prostaglandin receptor) agonists such as latanoprost, (5E)-7-{(1R,2R,3R,5S)-3,5-dihydroxy-2-[(3R)-3-hydroxy-5-phenylpentyl]cyclopentyl}hept-5-enoic acid, bimatoprost, travoprost, unoprostone and butaprost; O-acyl derivatives obtained by partial or total esterification of vitamin F with glucose, as described in patent application EP 1 688 128; 15-hydroxy-prostaglandin dehydrogenase inhibitors; mixtures thereof.

As other additional active compounds for promoting the growth and/or limiting the loss of keratin fibres such as the hair and the eyelashes, which may be used in combination with the compound of formula (I), mention may be made of pyridinedicarboxylate derivatives or a salt thereof, such as those described in patent application EP 1 352 629 and more particularly diethyl 2,4-pyridinedicarboxylate.

Advantageously, the composition according to the invention comprises at least one compound of formula (I) as defined above and at least one prostaglandin or prostaglandin derivative, for instance the prostaglandins of series 2 especially including PGF2-α and PGE2 in acid, salt or ester form (for example the isopropyl esters), derivatives thereof, for instance 16,16-dimethyl PGE2, 17-phenyl PGE2, 16,16-dimethyl PGF2-α, 17-phenyl PGF2-α, prostaglandins of series 1, for instance 11-deoxyprostaglandin E1,1-deoxy-prostaglandin E1 in acid, salt or ester form, analogues thereof, especially latanoprost, (5E)-7-{(1R,2R,3R,5S)-3,5-dihydroxy-2-[(3R)-3-hydroxy-5-phenylpentyl]cyclo-pentyl}hept-5-enoic acid, viprostol, bimatoprost, cloprostenol, travoprost, fluprostenol, cloprostenol, butaprost, unoprostone, misoprostol, and the salts or esters thereof.

The composition preferably contains at least one non-prostanoic EP2 and/or EP4 receptor agonist as described especially in EP 1 175 892.

In a particularly preferred manner, the additional active compound will be chosen from aminexil, minoxidil, O-acyl derivatives obtained by partial or total esterification of vitamin F with glucose; latanoprost, (5E)-7-{(1R,2R,3R,5S)-3,5-dihydroxy-2-[(3R)-3-hydroxy-5-phenylpentyl]cyclopentyl}hept-5-enoic acid, butaprost, bimatoprost, travoprost and diethyl 2,4-pyridinedicarboxylate, or mixtures thereof.

It may also be envisaged for the composition comprising at least the compound of formula (I) to be in liposomal form, as described especially in document WO 94/22468. Thus, the compound encapsulated in the liposomes may be delivered selectively to the hair follicle.

The composition according to the invention may be applied to the alopecic areas of the scalp and the hair of an individual, and optionally left in contact for several hours and optionally rinsed off.

The composition containing an effective amount of a compound of formula (I), salified or non-salified, solvated or non-solvated, may, for example, be applied in the evening, kept in contact throughout the night and optionally shampooed out in the morning. These applications may be repeated daily for one or more months according to the individual.

Advantageously, in the process according to the invention, between 5 µL and 500 µL of a solution or composition as defined above, comprising from 0.001% to 5% of compound of formula (I), are applied to the areas of the scalp to be cared for or treated.

Exemplary embodiments of the invention, which shall not limit its scope in any way, will now be given by way of illustration.

Example 1

Hair-Loss Counteractant Lotion

Sodium salt of 3-hydroxy-2-pentylcyclopentane-acetic acid as a 30% solution in a water/dipro-pylene glycol mixture (70/30) 2%

Ethanol/propylene glycol/H$_2$O mixture (50/20/30) qs 100%

This lotion is applied to the scalp once or twice a day, at a rate of 1 ml per application.

Evaluation of the Antioxidant Potential: DCFH-DA Test

The sodium salt of 3-hydroxy-2-pentylcyclopentane-acetic acid is used as a 30% solution in a water/dipropylene glycol mixture (70/30).

In a model of human epidermoid keratinocytes in culture (HaCaT) exposed to UV radiation, the global oxidative stress effect of the said compound after oxidation of a fluorescent probe (DCFH-DA) is measured.

The use of DCFH-DA as a marker of intracellular global oxidative stress is based on its physicochemical properties. It is a nonionic apolar molecule that is capable of diffusing across cell membranes. Once inside the cell, DCFH-DA is hydrolysed by intracellular esterases to a non-fluorescent compound: DCFH or 2,7-dichlorofluorescine. In the presence of activated oxygen species (H$_2$O$_2$; OH°), DCFH is rapidly oxidized to a highly fluorescent compound: DCF or 2,7-dichlorofluorescein.

HaCaT keratinocytes pretreated with the active agents for 24 hours are rinsed with PBS+ and incubated in the presence of DCFH-DA [20 µM] for 30 minutes at 37° C. in the dark.

After removal of the probe, the cells are exposed to 2 J/cm$^2$ of UVA (WG335 filter) in the presence of 1 ml/well of PBS+.

The DCF fluorescence is evaluated immediately after the UVA exposure, by spectrofluorimetry (excitation 480 nm; emission 530 nm).

Preliminary tests made it possible to detect an antioxidant potential with protection against oxidative stress of the starting material comprising the sodium salt of 3-hydroxy-2-pentylcyclopentaneacetic acid as a 30% solution in a water/dipropylene glycol mixture (70/30).

The invention claimed is:

1. Cosmetic process for inducing and/or stimulating growth of the eyelashes and/or halting their loss and/or increasing their density, which comprises applying on the eyelashes and/or eyelids of a subject in need thereof a mascara composition comprising in a physiologically acceptable medium, an amount effective for inducing and/or stimulating growth of the eyelashes and/or halting their loss and/or increasing their density of at least one jasmonic acid derivative of formula (I) below:

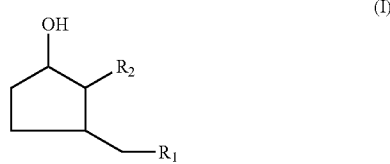

(I)

in which:
$R_1$ represents a radical $COOR_3$,
$R_3$ denoting a hydrogen atom or a $C_1$-$C_4$ alkyl radical, optionally substituted with one or more hydroxyl groups or a pentyl, pentenyl, hexyl or heptyl radical,
$R_2$ represents a linear saturated or unsaturated hydrocarbon-based radical containing from 1 to 18 carbon atoms, or a branched or cyclic saturated or unsaturated hydrocarbon-based radical containing from 3 to 18 carbon atoms, and/or an optical isomer thereof and/or a salt thereof, and leaving said composition in contact on the eyelashes and/or eyelids.

2. Cosmetic process for inducing and/or stimulating growth of the eyelashes and/or halting their loss and/or increasing their density according to claim 1, wherein $R_1$ denotes a radical chosen from —COOH, —COOMe, —COO—$CH_2$—$CH_3$, —COO—$CH_2$—CH(OH)—$CH_2$OH, —COO$CH_2$—$CH_2$—$CH_2$OH and —COO$CH_2$—CH(OH)—$CH_3$.

3. Cosmetic process for inducing and/or stimulating growth of the eyelashes and/or halting their loss and/or increasing their density according to claim 2, wherein $R_1$ denotes a radical —COOH.

4. Cosmetic process for inducing and/or stimulating growth of the eyelashes and/or halting their loss and/or increasing their density according to claim 1, wherein $R_2$ denotes a saturated or unsaturated linear hydrocarbon-based radical.

5. Cosmetic process for inducing and/or stimulating growth of the eyelashes and/or halting their loss and/or increasing their density according to claim 1, wherein the compound of formula (I) is chosen from 3-hydroxy-2-[(2Z)-2-pentenyl]cyclopentaneacetic acid or 3-hydroxy-2-pentyl-cyclopentaneacetic acid or a corresponding salt thereof.

6. Cosmetic process for inducing and/or stimulating growth of the eyelashes and/or halting their loss and/or increasing their density according to claim 1, wherein said composition does not include any additional active compound for promoting the growth of keratin fibres and/or for limiting their loss.

7. Cosmetic process for inducing and/or stimulating growth of the eyelashes and/or halting their loss and/or increasing their density according to claim 1, wherein said at least one jasmonic acid derivative of formula (I) is a salt thereof selected from the group consisting a salts of an alkali metal; a salt of an alkaline-earth metal; an ammonium salt of formula $NH_4^+$; a quaternary ammonium salt; a salt of an organic amine; a lysine salt and an arginine salt.

8. Cosmetic process for inducing and/or stimulating growth of the eyelashes and/or halting their loss and/or increasing their density according to claim 1, wherein said at least one jasmonic acid derivative of formula (I) is a sodium salt thereof.

* * * * *